(12) United States Patent
Farina et al.

(10) Patent No.: US 7,973,066 B2
(45) Date of Patent: Jul. 5, 2011

(54) PYRROLO[1,2-A]IMIDAZOLEDIONE EFFECTIVE IN THE TREATMENT OF PERIPHERAL NEUROTOXICITY INDUCED BY CHEMOTHERAPEUTIC AGENTS

(75) Inventors: Carlo Farina, Milan (IT); Carla Ghelardini, Pistoia (IT); Paola Petrillo, Milan (IT)

(73) Assignee: Neurotune AG, Schlieren (CH)

( * ) Notice: Subject to any disclaimer, the term of this patent is extended or adjusted under 35 U.S.C. 154(b) by 144 days.

(21) Appl. No.: 12/312,575

(22) PCT Filed: Nov. 14, 2007

(86) PCT No.: PCT/EP2007/062323
§ 371 (c)(1),
(2), (4) Date: May 14, 2009

(87) PCT Pub. No.: WO2008/058988
PCT Pub. Date: May 22, 2008

(65) Prior Publication Data
US 2010/0062077 A1     Mar. 11, 2010

(30) Foreign Application Priority Data
Nov. 15, 2006   (EP) .................................. 06124142

(51) Int. Cl.
*A61K 31/4166* (2006.01)
*C07D 235/00* (2006.01)

(52) U.S. Cl. ................... 514/387; 548/301.7; 548/302.7; 514/385; 514/386

(58) Field of Classification Search ............... 548/301.7, 548/302.7; 514/385, 386, 387
See application file for complete search history.

(56) References Cited

U.S. PATENT DOCUMENTS
7,544,705 B2 *  6/2009  Farina et al. ................... 514/387
7,732,473 B2 *  6/2010  Farina et al. ................... 514/387

FOREIGN PATENT DOCUMENTS
WO    WO2004085438    10/2004

OTHER PUBLICATIONS

Robert Cavaliere, MD. et al, "Neurologic Toxicities of Cancer Therapies", Current Neurology and Neuroscience Reports 2006, 6:218-226.
International Search Report of PCT/EP2007/062323 dated Jul. 2, 2008.
Frederick H. Hausheer et al.; "Diagnosis, Management, and Evaluation of Chemotherapy-Induced Peripheral Neuropathy"; Seminars in Oncology; vol. 33, No. 1, Feb. 2006; pp. 15-49.
Mark Stillman MD and Juan P. Cata, MD; "Management of Chemotherapy-induced Peripheral Neuropathy"; Current Pain and Headache Reports 2006; vol. 10, No. 4, Aug. 2006; pp. 279-287.
Guido Cavaletti and Paola Marmiroli; "Chemotherapy-induced peripheral neurotoxicity"; Expert Opinion on Drug Safety Nov. 2004; vol. 3, No. 6, Nov. 2004; pp. 535-546.
Sarah J.L. Flatters, Gary J. Bennett; "Ethosuximide reverses paclitaxel-and vincristine-induced painful peripheral neuropathy"; Pain 109; 2004; pp. 150-161.
Stefan Quasthoff, Hans Peter Hartung; "Chemotherapy-induced peripheral neuropathy"; J Neurol (2002); pp. 9-17.

* cited by examiner

*Primary Examiner* — Golam M Shameem
(74) *Attorney, Agent, or Firm* — Abelman, Frayne & Schwab

(57) ABSTRACT

The use of a compound of formula (I), is disclosed in treating and/or preventing 5 chemotherapy-induced peripheral neurotoxicity (CIPN). The invention includes pharmaceutical compositions wherein the compound of formula (I) is present in a mixture with anticancer agents. An improved anticancer treatment with reduced CIPN-related side effects is also provided.

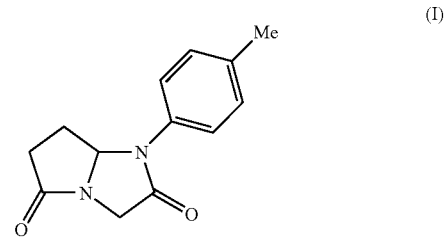

(I)

9 Claims, 5 Drawing Sheets

PYRROLO[1,2-A]IMIDAZOLEDIONE EFFECTIVE IN THE TREATMENT OF PERIPHERAL NEUROTOXICITY INDUCED BY CHEMOTHERAPEUTIC AGENTS

FIELD OF THE INVENTION

The present invention relates to the field of anticancer therapy, addressing the problem of reducing neurotoxic side effects of chemotherapeutic agents.

BACKGROUND OF THE INVENTION

Treatment with different chemotherapeutic agents, such as vincristine, taxol or oxaliplatin, causes in most cases the development of dose-limiting chronic neurotoxicity. The toxic damage is made evident by ensuing neural dysfunctions such as mechanical and cold allodynia, ongoing burning pain, myalgias, tingling, numbness, etc. (Cavaliere R. and Schiff D. 2006, Curr. Neurol. Neurosci. Rep. 6:218-26). The resulting pathological condition is also known as chemotherapy-induced peripheral neurotoxicity (CIPN). CIPN often represents the most important cause of discomfort and suffering in patients undergoing chemotherapy, which strongly limits the practical applicability of the latter. In patients with CIPN symptoms, the interruption of chemotherapy is no valid solution: this exposes to tumour worsening, whereas neurotoxicity is not necessarily removed, as it may persist or even develop after discontinuation of medication. The degree of severity of CIPN depends not only from the drug, time and dose used but also from the total cumulative dose applied.

Depending on the substance used, a pure sensory syndrome (with cisplatin, oxaliplatin, carboplatin) or a mixed sensorimotor neurotoxicity with or without involvement of the autonomic nervous system (vincristine, taxol) can ensue. In addition, the previous administration or co-treatment with two or more neurotoxic agents further increases the incidence and severity of neurotoxic effects. For example, cisplatin alone induced neurotoxic effects in 49% of patients (Bacon M. and et al. 2003, Int. J. Gynecol. Cancer 13:428-34), whereas when co-administered with paclitaxel, sensory neurotoxicity was observed in 91% of patients. These effects may lead to disability and worsening of life quality in the absence of tumor progression and it represents a serious dose-limiting side effect.

In addition, the development of the neurotoxic syndrome can interfere with optimal drug dosing, delay sequencing of therapy, or necessitate the discontinuation of treatment.

Little is known about the mechanism responsible for the development of CIPN and to date no satisfactory therapies are available (Quasthoff S. and Hartung H. P. 2002, J. Neurol. 249:9-17).

Attempts have been made to address the symptoms with drugs efficacious on pain of various origins. For example the tricyclic antidepressant nortriptyline, known to be efficacious in treating pain of different origins and diabetic associated neuropathies, was tested in a double-blind, placebo-controlled trial to establish its ability to treat a cisplatin-induced pain syndrome (Hammack J. E. et al. 2002 Pain 98:195-203). The study included 51 patients and the nortriptyline maximum dose was 100 mg/day. Global statistical analysis of the trial results pointed out the lack of nortriptyline efficacy over placebo. Lamotrigine, a drug that reduces neuronal hyperexcitability, failed to reduce CIPN in phase III clinical trials (Renno S. I. et al. 2006, J. Clin. Oncol. 2006, ASCO Annual Meeting Proceeding Part I Vol 24, No. 18S:8530). All the patients showed severe neurotoxic symptoms induced by treatment with vinca alkaloids (30%), taxanes (25%), platinum-agents (7%), chemotherapy combinations (34%), and others (3%). After 10 weeks of therapy, the average scores were similar between the lamotrigine and placebo treated groups. Gabapentin is an anticonvulsant used for various neuropathies and neuralgias; (Rowbotham M. et al. 1998, JAMA 280:1837-1842; Backonja M. et al. 1998, JAMA 280:1831-1836). This compound, tested on cancer patients with CIPN (Wong G. Y. 2005, J. Clin. Oncol. 2005, ASCO Annual Meeting Proceeding Part I Vol 23, No. 16S:8001), failed to reduce pain intensity (NRS score), sensory neuropathy (ECOG rating), and other adverse events. In addition, patients treated with gabapentin reported significant more adverse side effects such as nystagmus and dizziness. Imidazole derivatives with general nootropic activity have been described in WO 2004/085438; these compounds were not used in association with chemotherapeutic agents and no neuroprotection or other beneficial effect in CIPN has been disclosed.

As summarised above, no effective therapy is currently available for chemotherapy-induced neurotoxicity. The need is thus felt for effective therapies in the treatment of CIPN. A particular need is that of a curative treatment, i.e. capable to treat the underlying cause, as the mere symptomatic treatment has so far failed to obtain appreciable results. The need is also felt for agents capable to improve the tolerability of chemotherapeutic therapy, thereby increasing the clinical acceptance of the latter. A further need is that of suitable co-therapies capable to positively synergise in the effective treatment of cancer, whereby the neurotoxic side-effects of chemotherapeutic agents are inhibited. It is also desired to dispose of pharmaceutical compositions suitable for co-therapy, whereby one agent inhibits the neurotoxic effect of the chemotherapeutic agent. A further need is that of agents capable to block neurotoxic effects of CIPN developing even after discontinuation of the chemotherapeutic agent.

SUMMARY

We have found that a compound represented by the formula (I)

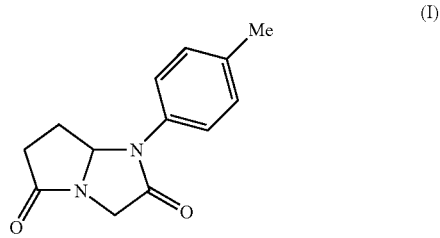

and solvates thereof is strongly effective in treating and preventing chemotherapy-induced neurotoxicity, while other compounds used in clinical practice to protect from chemotherapy-induced neuropathy and neuralgias, performed much less effectively or even failed to show a curative effect when tested under the same conditions.

The present invention is thus directed to the use of the compound of formula (I) and solvates thereof, in the treatment and/or prevention of chemotherapy-induced neurotoxicity. The invention also extends to the use of an association of a compound of formula (I) or solvates thereof with a chemotherapeutic agent, in the treatment of cancer. The invention further comprises pharmaceutical compositions wherein a compound of formula (I) or solvates thereof is present in association with a chemotherapeutic agent.

DETAILED DESCRIPTION OF THE INVENTION

Figure 1:
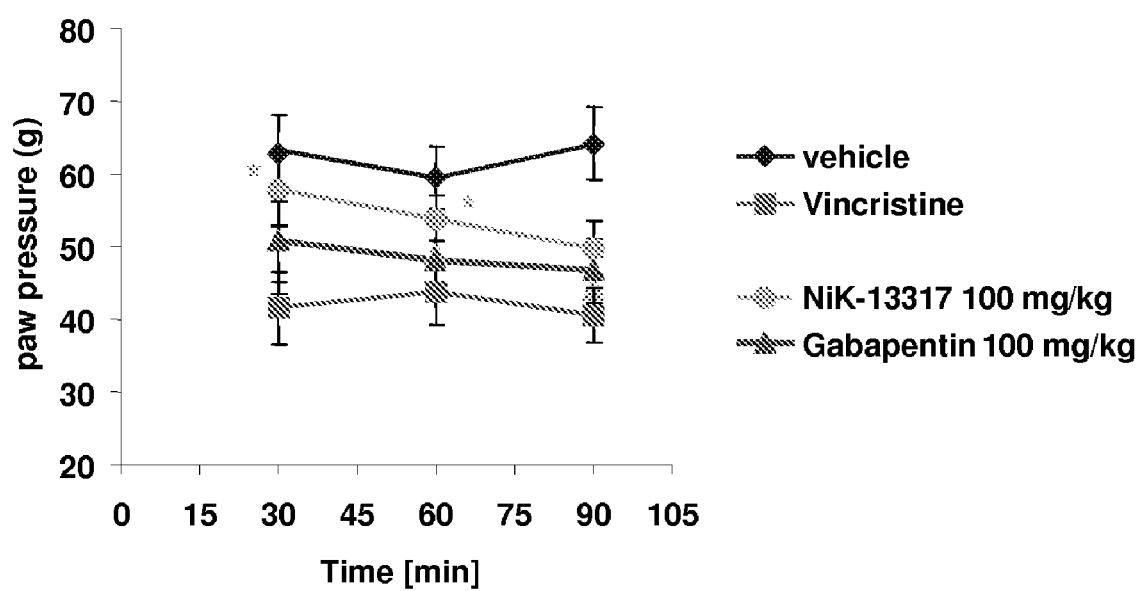
FIG. 1. Vincristine-induced peripheral neuropathy, paw pressure: Effect of NiK-13317 and gabapentin given p.o.
*$p<0.01$ in comparison versus vincristine/vehicle treated rats. Each value represents the mean of 8 rats. Test was performed 4 days after the last vincristine injection FIG. 2. Vincristine-induced peripheral neuropathy, paw pressure: repeated treatment (i.p., 5 days).
^$p<0.05$ and *$p<0.01$ in comparison with vincristine/vehicle treated rats. Each value represent the mean of 8 rats. Compounds (30 mg/kg i.p.) were administered daily during the last five days of vincristine protocol. Test was performed 4 days after the last vincristine injection.

A first object of the present invention is the use of a compound of formula (I)

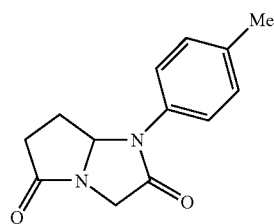

(I)

or a solvate thereof, in the manufacture of a medicament useful for treating and/or preventing chemoterapeutic-induced neurotoxicity.

The compound (I) is effective in particular in reducing the various neurotoxic effects of chemotherapeutic agents such as mechanical and cold allodynia, ongoing burning pain, myalgias, tingling, numbness, etc. The invention also includes a method of treating chemoterapeutic-induced neurotoxicity, involving the administration of a compound of formula (I) to a patient in need thereof. Further part of the invention are the said compound (I), or its pharmaceutical compositions, for use in treating and/or preventing chemoterapeutic-induced neurotoxicity.

In the formula (I) the symbol Me means $CH_3$. The compound of formula (I), namely 1-(4-Methylphenyl)dihydro-1H-pyrrolo[1,2-a]imidazole-2,5(3H,6H)-dione can be used in the form of its isolated (S) or (R) enantiomers or mixtures thereof in any proportions, including the racemic mixtures, i.e. wherein the two enantiomers are present in equal amount; said enantiomers are (S)-1-(4-Methylphenyl)dihydro-1H-pyrrolo[1,2-a]imidazole-2,5(3H,6H)-dione (also identified herein as NiK-16140), and (R)-1-(4-Methylphenyl)dihydro-1H-pyrrolo[1,2-a]imidazole-2,5(3H,6H)-dione (also identified herein as NiK-16139); the racemic mixture of said enantiomers is herein identified as NiK-13317.

The administration dosage of compound (I) can be varied according to the severity of the neurotoxicity to be treated, the route of administration, the type of chemotherapeutic agent in use, the patient condition, etc. As a non-limitative reference, pro-Kg (per Kg of body weight) daily dosages are comprised between 0.5 and 50 mg.

As documented in the experimental part, the present compound was found highly effective in rats treated with various chemotherapeutic agents and bearing the symptoms of CIPN, whereas drugs like gabapentin, currently used to address these side effects, proved much less effective or even showed no activity. The herein documented efficacy of compound (I), with respect to different types of anticancer agents demonstrates the widespread applicability of the present use with respect to anticancer therapy.

In addition, the compound of formula (I) did not affect the efficacy of anticancer treatments as reported in the experimental part.

The present invention finds thus substantial utility in improving the practical applicability of current anticancer (chemotherapy) therapies, in that it reduces the associated CIPN side effects and improves patient's acceptability of the anticancer treatment.

The compound of formula (I) is preferably administered in conjunction with the anticancer chemotherapeutic drug: this can be effected either by separate administrations of the two compounds, or by administration of a single dosage unit comprising an admixture of the two compounds.

The compound of formula (I) can also be used in advance to an anticancer chemotherapeutic treatment, so as to prevent the development of CIPN. In this case the treatment with compound (I) is started before the anticancer treatment and possibly continues jointly therewith.

The compound of formula (I) are also useful in treating possible CIPN symptoms developing after conclusion of the treatment with anticancer chemotherapeutic drugs; in this case the treatment with compound (I) is started (or continued) after conclusion of the anticancer treatment.

The compound of formula (I) was also found not to develop tolerance, which is of fundamental importance for the pathology in point, where the therapeutic intervention needs being continued over a long period of time.

A further object of the present invention is the use of an association of a compound of formula (I) as above described or a solvate thereof, with one or more anticancer chemotherapeutic agents, in the manufacture of a medicament for the treatment of cancer, said treatment being advantageously free from peripheral neurotoxicity side-effects.

The compound of formula (I) is known per se and can be prepared as described in WO 2004/085438, herein incorporated by reference.

A further object of the invention is a pharmaceutical composition comprising said compound of formula (I) in association with one or more anticancer chemotherapeutic agents, in the optional presence of pharmaceutically acceptable excipients. No limitation is present with respect to the type of anticancer chemotherapeutic agent to be used in association with the compound of formula (I); suitably, they can be chosen among those currently used in the medical practice; the invention is most useful when associated to those chemotherapeutic agents exerting the highest neurotoxic stimula. Example of anticancer chemotherapeutic agents to be used in association with the compound of formula (I) are organometallic compounds e.g. cis-platin, carbo-platin, oxaliplatin, ruthenium compounds, etc., Vinca alkaloids e.g. vincristine, vinblastine, taxol derivatives e.g. paclitaxel.

The compound of formula (I) is present in the pharmaceutical compositions in any amounts suitable for the needed treatment; indicative amounts range between 10 and 2500 mg, preferably between 50 and 1000 mg, most preferably between 100 and 500 mg.

The anticancer chemotherapeutic agent, if present, is used in any amounts suitable for the needed treatment.

The pharmaceutical compositions of the invention can be adapted for the various administration routes, and be provided for example in the form of injectable solutions, solutions for infusion, solutions for inhalation, suspensions, emulsions, syrups, elixirs, drops, suppositories, tablets, coated tablets, hard or soft capsules, microcapsules, granules, microgranules, pellets, dispersible powders, lotions, creams, ointments, medicated patches, etc. These compositions also include sustained release formulations.

The excipients optionally present in these compositions are those commonly used in pharmaceutical technology; they can be used in the manner and quantity commonly known to the expert of the art.

Solid administration forms, such as tablets and capsules for oral administration, are preferably supplied in dosage units.

The compositions may contain conventional excipients such as binders, fillers, diluents, tabletting agents, lubricants, detergents, disintegrants, colorants and wetting agents and can be coated in accordance with methods well known in the art.

The fillers include for example cellulose, mannitol, lactose and similar agents. The disintegrants include starch, polyvinylpyrrolidone and starch derivatives such as sodium starch glycolate; the lubricants include, for example, magnesium stearate; the wetting agents include for example sodium lauryl sulfate.

These solid oral compositions can be prepared with conventional mixing, filling or tabletting methods. The mixing operations can be repeated to disperse the active agent in compositions containing large quantities of fillers.

The liquid compositions can be provided as such or in the form of a dry product to be reconstituted with water or with a suitable liquid carrier at the time of use. The liquid compositions can contain conventional additives such as suspending agents, for example sorbitol, syrup, methylcellulose, gelatin, hydroxyethylcellulose, carboxymethylcellulose, aluminium stearate gel or hydrogenated edible fats, emulsifying agents, for example lecithin, sorbitan monooleate; non aqueous carriers (which can include edible oil) for example almond oil, fractionated coconut oil, oily esters such a glycerin esters, propylene glycol or ethyl alcohol; preservatives, for example methyl or propyl p-hydroxybenzoate or sorbic acid and if desired, conventional flavours or colorants.

For parenteral administration, fluid dosage units can be prepared containing the active compounds and a sterile carrier. The active compounds, depending on the carrier and concentration, can be suspended or dissolved. The parenteral solutions are normally prepared by dissolving the compound in a carrier and sterilizing by filtration, before filling suitable vials or ampoules and sealing. Adjuvants such as local anaesthetics, preservatives and buffering agents can be advantageously dissolved in the carrier. In order to increase stability, the composition can be frozen after filling the vial and the water removed under vacuum. The parenteral suspensions are prepared essentially in the same way, with the difference that the active compounds can be suspended rather than dissolved in the carrier, and can be sterilized by exposure to ethylene oxide prior to being suspended in the sterile carrier. A surfactant or humectant can be advantageously included to facilitate uniform distribution of the active compounds. For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences-Dekker) or Harrys Cosmeticology (Leonard Hill Books). As is the common practise, the compositions are normally accompanied by written or printed instructions, for use in the treatment concerned.

The invention is now illustrated by the following non-limiting examples.

EXPERIMENTAL PART

Example 1

Synthesis of (S)-1-(4-Methylphenyl)dihydro-1H-pyrrolo[1,2-a]imidazole-2,5(3H,6H)-dione (NiK-16140)

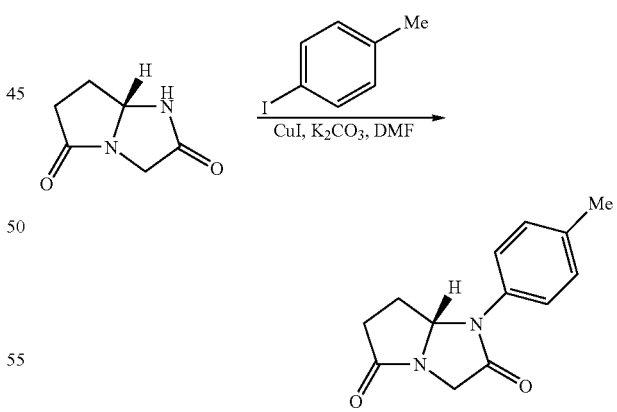

In a 100 ml round bottomed flask fitted with a magnetical stirrer and a reflux condenser are placed 10 ml of dimethylformamide, 1.2 g of (R)-dihydro-1H-pyrrolo[1,2-a]imidazole-2,5(3H,6H)-dione, 0.456 g of copper iodide, 1.2 g of potassium carbonate and 4.0 g of 1-iodo-4-methyl-benzene. The well stirred reaction mixture is heated at reflux for 4 hours. After cooling, the solvent is removed under vacuum (50° C., 7 mbar) and the residue is treated with 70 ml of ethyl acetate and the insoluble is filtered off. The organic solvent is then washed with 20 ml of saturated NaCl solution, dried over $Na_2SO_4$, filtered and evaporated under vacuum. The residue is triturated with 30 ml of diethyl ether and then crystallized with 20 ml of isopropanol, obtaining 0.92 g (y=47%) of the title compound as an off-white powder.

mp: 149-150° C.

$[\alpha]_D$: +138.2 (c=0.4, MeOH)

IR and $^1$H-NMR matched those of the corresponding racemate

Example 2

Synthesis of (R)-1-(4-Methylphenyl)dihydro-1H-pyrrolo[1,2-a]imidazole-2,5(3H,6H)-dione (NiK-16139)

The title compound was obtained following the procedure described in Example 1, starting from (S)-dihydro-1H-pyrrolo[1,2-a]imidazole-2,5(3H,6H)-dione.

mp: 150-151° C.

$[\alpha]_D$: −139.9 (c=0.4, MeOH)

IR and $^1$H-NMR matched those of the corresponding racemate

Example 3

Synthesis of racemic 1-(4-Methylphenyl)dihydro-1H-pyrrolo[1,2-a]imidazole-2,5(3H,6H)-dione (NiK-13317)

This compound was obtained following the procedure described in Example 1, starting from racemic dihydro-1H-pyrrolo[1,2-a]imidazole-2,5(3H,6H)-dione.

mp: 131-132° C.

$^1$H-NMR (300 MHz, $CDCl_3$, δ ppm): 7.27 (d, 2H); 7.24 (d, 2H); 5.79 (m, 1H); 4.45 (d, 1H); 3.73 (d, 1H); 2.72 (ddd, 1H); 2.70 (m, 1H); 2.47 (dd, 1H); 2.38 (s, 3H); 2.08-1.98 (m, 1H).

IR (nujol, $cm^{-1}$): 1722, 1515, 1376, 1328.

Example 4

In-Vivo Pharmacological Testing

With the aim to detect the neuroprotective effects of the compound of formula (I) on CIPN, we have developed different rat models of this pathology, using three different systemic dosing schedules of vincristine, paclitaxel and oxaliplatin. For comparison, the anti-hyperalgesic drug gabapentin, a compound clinically used in treating CIPN, was tested with the same protocols.

Peripheral neuropathies were induced in rats (adult Sprague Dawley, 150-200 g), by repeated administration of vincristine, taxol and oxaliplatin using the following treatment schedules.

Vincristine was administered i.v. (150 μg/kg), every two days until a cumulative dose of 750 μg/kg was reached. Paw mechanical iper-sensitivity was evaluated 4 days after the last vincristine injection (Marchand F. et al. 2003, Brain Res. 980:117-120).

Taxol neuropathy was induced by i.p. administration (0.5 mg/kg) once a day, on days 1, 3, 5, 8. Cumulative taxol dose was 2 mg/kg. The pharmacological test was performed 14-18 days after the last taxol injection (Polomano R. C. et al. 2001, Pain 94:293-304).

Oxaliplatin was administered at the dose of 2.4 mg/kg for 5 consecutive days every week, for three weeks (15 i.p. injection). The cumulative dose of oxliplatin was 36 mg/kg (Cavaletti G. et al. 2001, Eur. J. Cancer 37:2457-2463). Test was performed 48 h after the last oxaliplatin injection.

When a chemotherapeutic injection was to be given on a same day as behavioural testing, rats were injected after the measurement was taken.

Paw mechanical iper-sensitivity was determined using a Randall & Selitto apparatus exerting a force that increases at constant rate (32 g/s) in agreement with Leighton G. E. et al. (1988, Br. J. Pharmacol 93:553-560). The stimulus at which rats withdraw the paw was evaluated before and at different times after drugs treatment. Results represent the mean of mechanical thresholds expressed as grams. To avoid any possible damage to the animal paw the maximum applied force was fixed at 240 g. The following result were obtained.

a. Vincristine-Induced Peripheral Neuropathy

The results are summarised in FIG. 1. Vincristine treatment produced a marked and prolonged mechanical hyperalgesia as evident from the reduction of mechanical paw pressure threshold of treated rats. A pronounced significant reversal of vincristine mechanical hyper-sensitivity was elicited by 100 mg/kg of compound of Example 3 (NiK-13317) given p.o after 30 and 60 min from compound's treatment (FIG. 1). Interestingly, gabapentin, given at the same dose, lacked of any significant effects. NiK-13317 and gabapentin were devoid of any significant activity on vehicle treated animals.

Figure 2:
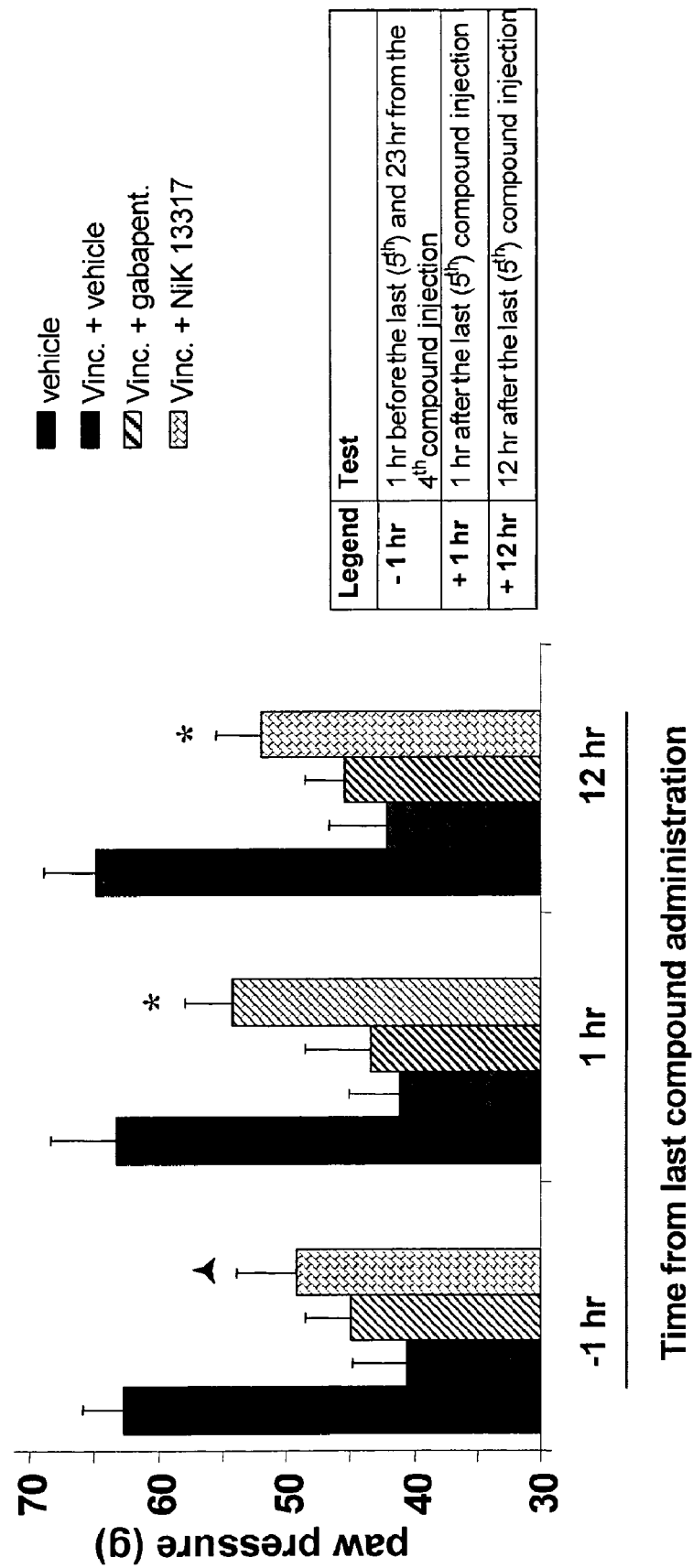

In sub-chronic experiments, gabapentin or NiK-13317 (both at 30 mg/kg; i.p.) were administered daily during the last five days of vincristine treatment. Paw pressure tests were performed 1 hr before and, 1 and 12 hr after the last compound's injection. After repeated treatment gabapentin had no significant effects on mechanical hyperalgesia at any times tested. NiK-13317 exhibited a statistically significant (p<0.01) anti-hyperalgesic effect 1 hr and 12 hr after the last administration, without development of tolerance (FIG. 2). Interestingly, NiK-13317 induced a statistically significant effect (p<0.05) also 23 hr after the $4^{th}$ administration.

b. Taxol-Induced Peripheral Neuropathy

Figure 3:
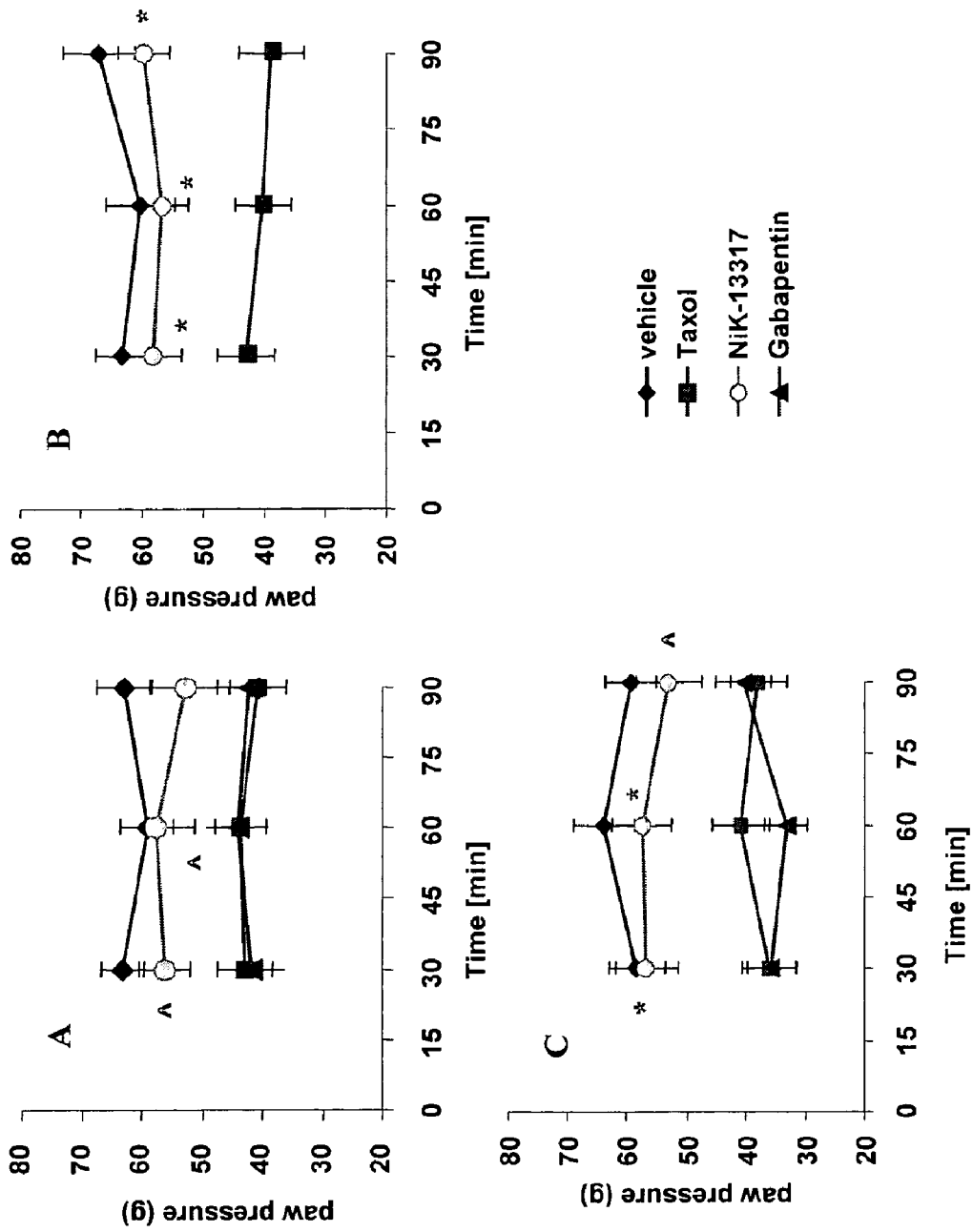
FIG. 3. Taxol-induced peripheral neuropathy, paw pressure test: Effect of NiK-13317 and gabapentin
Test compounds were administered p.o. at 100 mg/kg p.o. A), i.p. at 30 mg/kg B) or i.v. at 3 mg/mg C). ^$p<0.05$ and *$p<0.01$ versus taxol-treated rats. Each value represents the mean of 8 rats. Test was performed 14-18 days after the last taxol injection.

Like vincristine, also taxol treatment produced a significant mechanical hyperalgesia. In this model, NiK-13317 (100 mg/kg given orally) significantly increased the rat paw pressure threshold 30 and 60 min after treatment. On the contrary, the reference standard gabapentin, in the same experimental conditions, was not able to induce any anti-hyperalgesic effect (FIG. 3A). This lack of efficacy was consistent with the previous data obtained using the vincristine hyperalgesia model. NiK-13317 is also active after i.p. (30 mg/kg) and i.v (3 mg/kg) at 30-90 min from administration. Gabapentin, given i.p. or i.v. lacked of any significant effect (FIGS. 3B and C, respectively).

c. Oxaliplatin-Induced Peripheral Neuropathy

Figure 4:
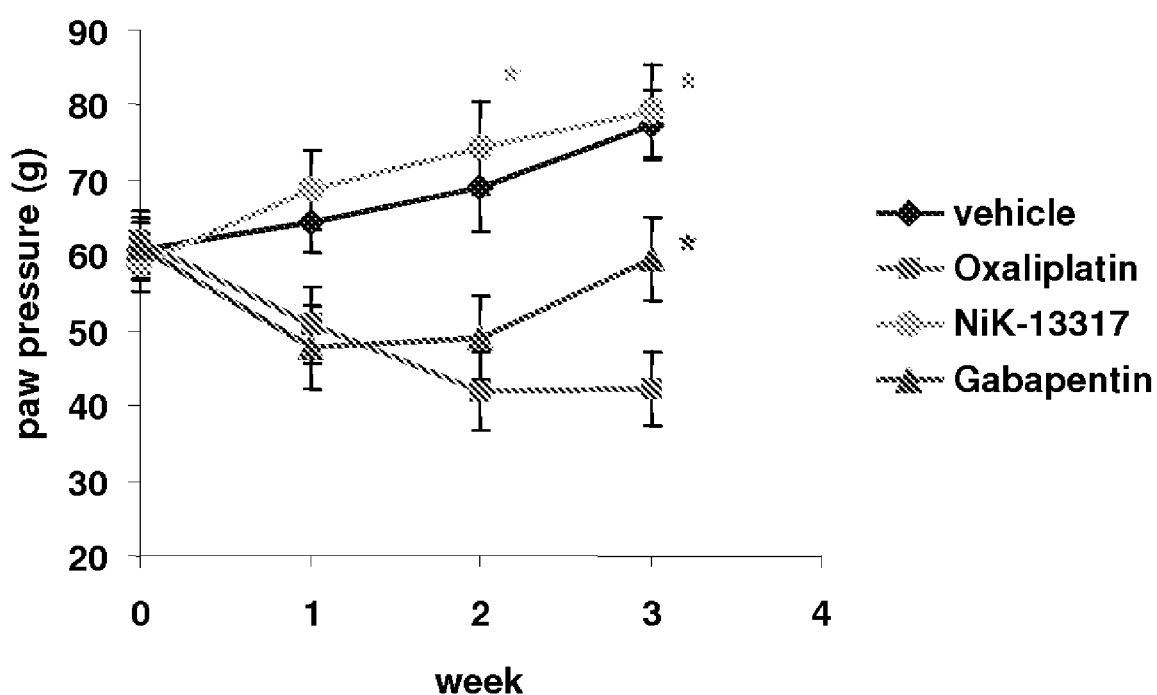
FIG. 4. Effect of gabapentin and NiK-13317 given p.o. during oxaliplatin-induced peripheral neuropathy development: paw pressure test. Test compounds were administered p.o. at 100 mg/kg once daily starting three days before oxaliplatin treatment and during the same days of chemotherapeutic injection. Test was performed 30 min after compounds administration. *$p<0.01$ versus oxaliplatin treated rats. Each value represents the mean of 11 rats.

Repeated administration of oxaliplatin caused a decrease in paw pressure threshold that is evident starting from the first week of treatment (FIG. 4). Maximum hyperalgesia was obtained after a two weeks period of treatment. NiK-13317 and gabapentin were repeatedly administered p.o. (100 mg/kg) once daily starting three days before oxaliplatin treatment. Compound administration was performed in the same days of chemotherapeutic injection. Rats were tested for mechanical hyperalgesia every week, 30 min after NiK-13317 administration and before oxaliplatin injection.

In these conditions NiK-13317 completely prevented oxaliplatin-induced decrease of mechanical threshold at all the time tested. Gabapentin administered with the same treatment schedule displayed only a moderated anti-hyperalgesic effect at the third week (FIG. 4).

Figure 5:
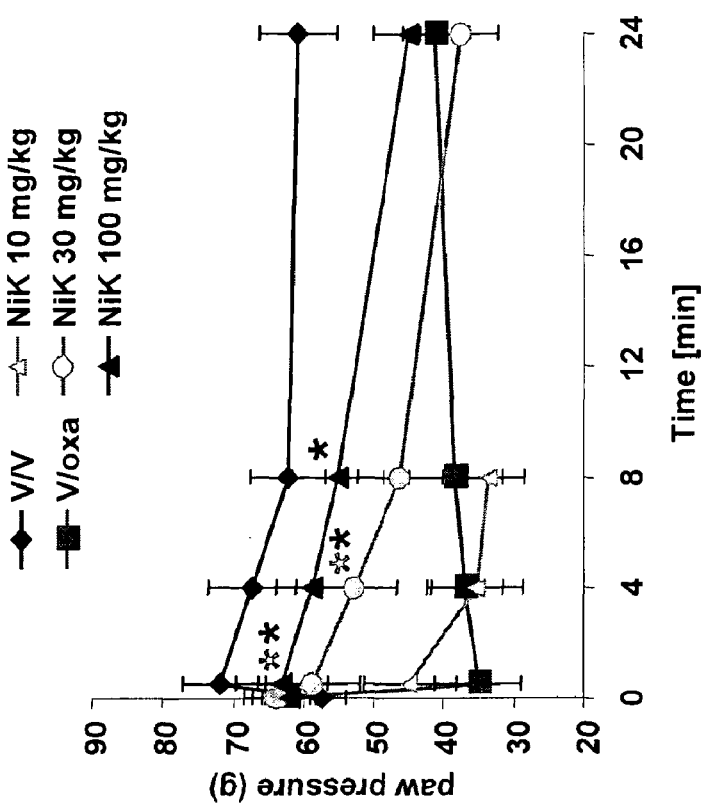
FIG. 5: Pharmacodynamic of gabapentin A) and NiK-13317 B) given p.o. on oxaliplatin-induced peripheral neuropathy: paw pressure test.
Test was performed 48 hr after the last oxaliplatin injection. Test compounds were administerd p.o. once daily starting three days before oxaliplatin treatment and during the same days of chemotherapeutic injection. *$p<0.01$ versus oxaliplatin treated rats. Each value represents the mean of 11 rats.
Figure 5:
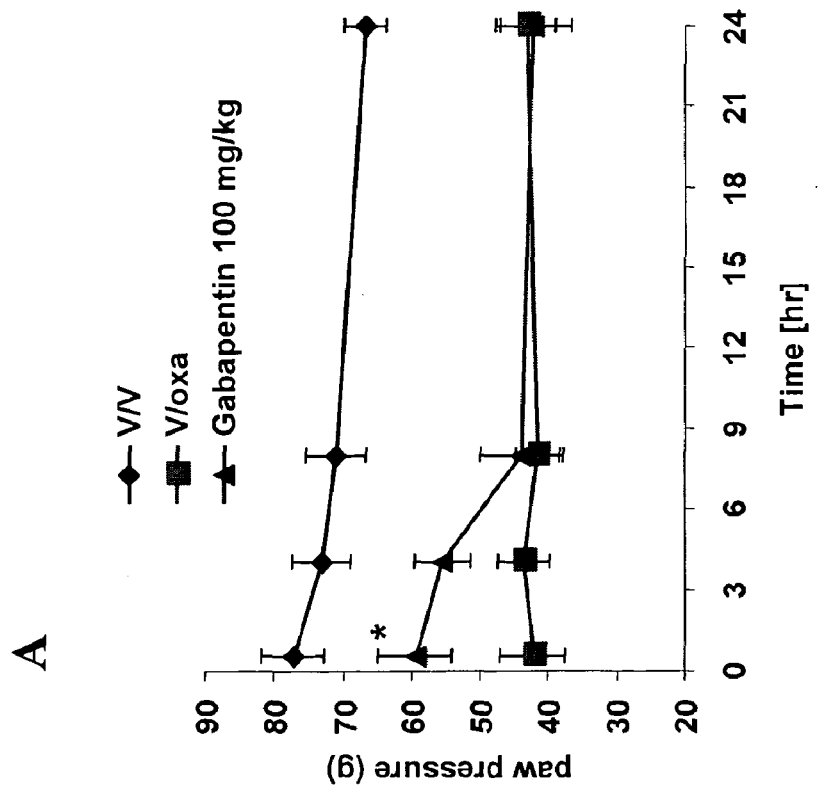

Pharmacodynamic experiments performed after 3 weeks of oxaliplatin treatment showed that NiK-13317 given orally was active at 30 min and 4 hr after compound's administration. At 100 mg/kg, the compound was still active after 8 hr of treatment (FIG. 5B). Interestingly, gabapentin displayed only a moderate effect after 30 min of treatment (FIG. 5A). Neither NiK-13317 or gabapentin induced significant effects on vehicle treated animals.

Similar results were obtained in tests using the (S) and (R) enantiomers of the compound of formula (I).

Example 5

In Vitro Combination Studies with Taxol, Oxaliplatin and Vincristine

In order to verify if the use of NiK-13317 for the treatment of CIPN would not affect the efficacy of anticancer treatments, the effect of NiK-13317 on cytotoxicity of known anticancer drugs was examined in vitro using HT29 human colon carcinoma cell line.

HT29 cells were plated (4000 cells/well) in 96-well tissue culture plates, and, after 24 h, treated with fixed concentrations of anticancer drugs (taxol, oxaliplatin and vincristine) alone or in combination with increasing concentrations of NiK-13317 (from 1 to 1000 µM). After 72 hours, cells were lysed and cell metabolic activity was quantified with ATPlite kit (Perkin Elmer Life Science) following manufacturer's recommendations. The ATP present in all metabolically active cells catalyses a reaction of transformation of D-luciferin by Luciferase, producing a luminescent signal measured using VICTOR³™ Multi Label Reader (Perkin Elmer). Results were expressed as percentage of luminescence produced (i.e. ATP produced) compared to the control. Complete concentration-response curves with anticancer drugs were constructed in order to identify the concentrations producing a submaximal and a maximal cytotoxic effect, to be utilized for combination experiments.

Taxol, vincristine and oxaliplatin produced a concentration-related cytotoxic effect with IC$_{50}$ values of 8 nM, 7 nM and 36 µM respectively, with a maximal effect observed at 100 nM for taxol and vincristine, and 100 µM for oxaliplatin, in agreement with literature data (Perego P et al. 2001, Cancer Res. 61:6034-7; Raymond E et al. 2002, Mol. Cancer. Ther. 1:227-35; Fogler W E et al. 1995, J. Natl. Cancer Inst. 87:94-104).

Results obtained in combination experiments clearly showed that NiK-13317 (from 1 to 1000 µM) did not modify any cytotoxic effect produced by all the anticancer drugs tested.

The invention claimed is:

1. A method for the treatment of chemotherapy-induced peripheral neurotoxicity, which comprises:
    administering to a patient in need thereof an effective amount of a compound of Formula (I)

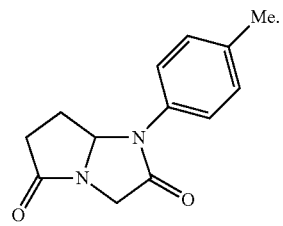

2. The method according to claim 1, wherein the compound of formula (I) is in the form of an isolated (S) or (R) enantiomer, or as a mixture thereof.

3. The method according to claim 1, wherein said neurotoxicity is induced by an anticancer chemotherapeutic agent selected from the group consisting of organometallic compounds, Vinca alkaloids, taxol, and derivatives thereof.

4. The method according to claim 2, wherein said neurotoxicity is induced by an anticancer chemotherapeutic agent selected from the group consisting of organometallic compounds, Vinca alkaloids, taxol, and derivatives thereof.

5. The method according to claim 3, wherein the anticancer chemotherapeutic agents is selected from the group consisting of cis-platinum, carbo-platinum, oxaliplatinum, ruthenium compounds, vincristine, vinblastine and paclitaxel.

6. The method according to claim 1, wherein the compound of formula (I) is administered in a pro-Kg amount comprised between 0.5 and 50 mg.

7. The method according to claim 2, wherein the compound of formula (I) is administered in a pro-Kg amount comprised between 0.5 and 50 mg.

8. The method according to claim 3, wherein the compound of formula (I) is administered in a pro-Kg amount comprised between 0.5 and 50 mg.

9. The method according to claim 4, wherein the compound of formula (I) is administered in a pro-Kg amount comprised between 0.5 and 50 mg.

* * * * *